United States Patent [19]

Broden

[11] Patent Number: 4,982,740

[45] Date of Patent: Jan. 8, 1991

[54] METHOD FOR USE IN THE HANDLING OF BODY FLUIDS

[76] Inventor: Bengt-Inge Broden, Gardfarivagen 3, S-532 00 Skara, Sweden

[21] Appl. No.: 371,769

[22] Filed: Jun. 27, 1989

Related U.S. Application Data

[62] Division of Ser. No. 230,374, Aug. 9, 1988, Pat. No. 4,935,020.

[30] Foreign Application Priority Data

Feb. 26, 1986 [SE] Sweden .................................. 8600852

[51] Int. Cl.[5] .............................................. A16B 5/00
[52] U.S. Cl. ...................................... 128/760; 604/415
[58] Field of Search ....................... 128/760, 762–765, 128/770, 771; 604/403, 407, 415

[56] References Cited

U.S. PATENT DOCUMENTS

| | | | |
|---|---|---|---|
| 3,066,672 | 12/1962 | Crosby et al. ........................ | 128/760 |
| 3,873,274 | 3/1975 | Neisius ................................ | 604/407 |
| 4,263,922 | 4/1981 | White .................................. | 128/763 |

FOREIGN PATENT DOCUMENTS

| | | | |
|---|---|---|---|
| 462602 | 1/1950 | Canada ................................ | 604/415 |
| 2402310 | 7/1974 | Fed. Rep. of Germany ...... | 604/415 |

*Primary Examiner*—Max Hindenburg
*Attorney, Agent, or Firm*—Sughrue, Mion, Zinn, Macpeak and Seas

[57] ABSTRACT

A method for use when making mutually different analyses on organic body fluids which, when taken as samples from a patient, are drawn into a so-called vacuum tube 1 which is hermetically sealed by means of a rubber stopper 2 or the like. The device comprises a pressure-equalizing and sample-retrieval cannula 3 having a penetrating pipe 4 with a pointed end intended to penetrate the rubber stopper 2. The other end of the pipe 4 merges with a seating for receiving a cuvette, pipette or like collecting vessel, provides with a suction hose 11 which extends through the pipe 4 and into the vacuum tube 1. The seating is an integral part of a holding device provided with downwardly projecting fixation means 6 which embrace the rubber stopper 2 and hold the cannula 3 in position, so as to enable the vacuum tube 1 to be centifuged with the cannula in position. The seating is constructed to guide accurately and hold firmly that end of the cuvette 9, 10 or pipette which coacts with the seating, so as to enable the vacuum tube 1 with the cuvette or pipette fitted thereto to be handled readily in the form of a unit and connected to a separate pump means 16 for drawing off fluid from the vacuum tube into the cuvette or pipette for analysis purposes.

6 Claims, 2 Drawing Sheets

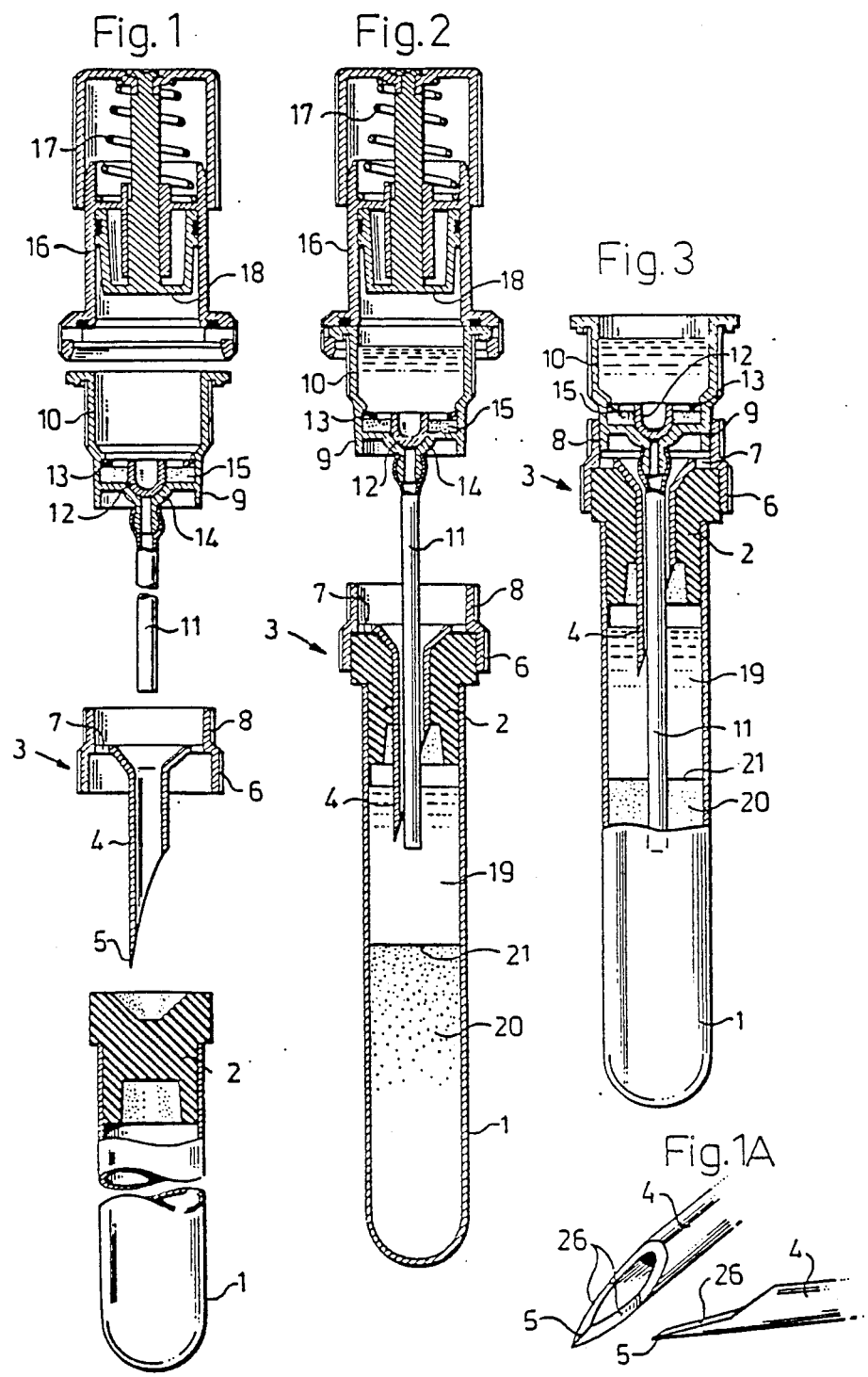

Fig. 4
Fig. 5
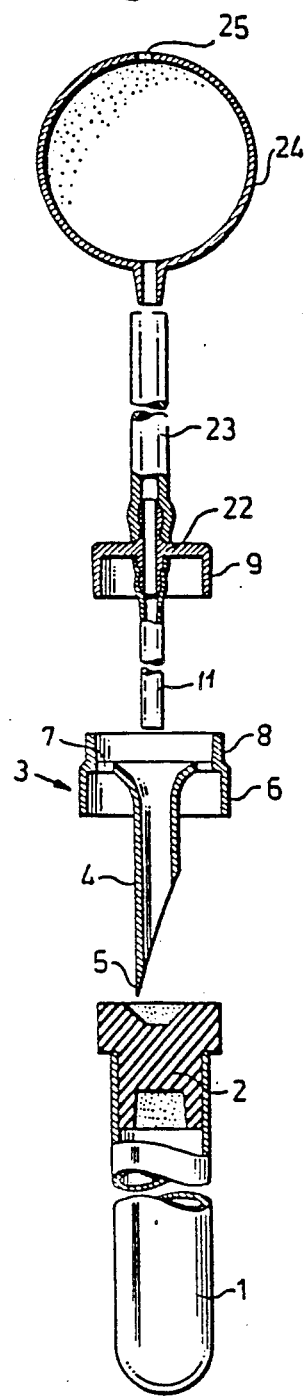
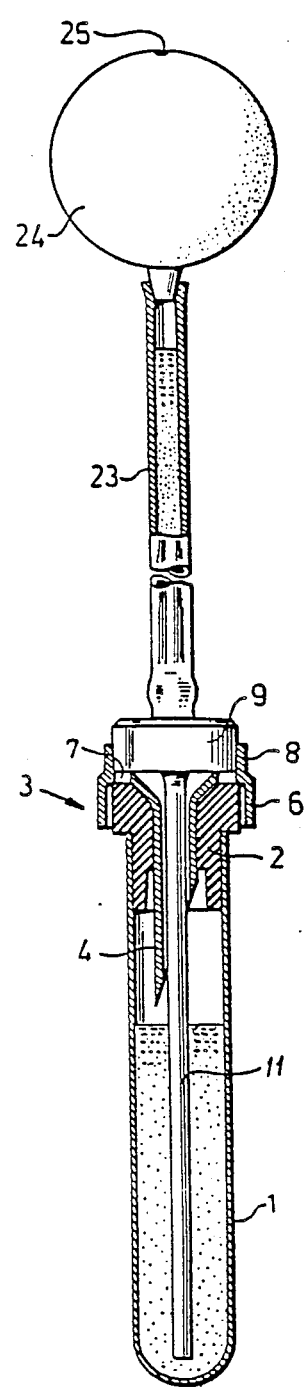

METHOD FOR USE IN THE HANDLING OF BODY FLUIDS

BACKGROUND OF THE INVENTION

This application is a divisional of U.S. application Ser. No. 230,374 filed Aug. 9, 1988, now U.S. Pat. No. 4,935,020.

The present invention relates to a method for use when analysing samples of organic body fluid that are drawn by suction from a patient into a so-called vacuum tube, which is held hermetically sealed with the aid of a rubber stopper or some corresponding sealing device.

A number of analyses are carried out daily on organic body fluids in hospital and like establishments, in order to establish the condition of the patients concerned. The majority of these analyses are carried out on blood serum and to this end there is first taken from the patient a small amount of his/her blood. The blood is normally taken with the aid of a so-called vacuum tube, i.e. a test tube which is sealed hermetically by means of a rubber stopper, in which a partial vacuum prevails. When the interior of the vacuum tube is placed in communication with a blood vessel, via a cannula, blood is automatically drawn into the tube by suction. The tube is then taken to a laboratory, or some like place, with the sealing stopper intact and with a partial vacuum still prevailing in the tube. In order to have access to the blood sample in the tube, it is necessary to remove the stopper. As a result of the air streams which flow past the stopper as the pressure in the tube is equalized by removal of the stopper, air mixed with blood fragments is liable to leave the tube and enter the ambient surroundings.

Part of the blood sample is normally extracted from the open vacuum tube with the aid of a pipette, comprising a cylindrical plastic plunger which is pressed down into the tube in sealing abutment with the inner wall surface thereof, so as to force blood into the pipette. If the plunger fails to seal precisely against the wall of the vacuum tube, blood is likely to spurt from the tube, around the sides of the plunger. Since the majority of analyses made on blood samples are carried out on blood serum, the sample must first be centrifuged in order to separate the blood serum from the blood corpuscles. Blood is also liable to spill during this procedure.

The aforedescribed blood-sample handling processes are unacceptable from the point of view of hygiene, since the laboratory personnel involved are in danger of being infected with diseases transmitted through the blood, for example such diseases as Aids and Yellow Fever. Moreover, the aforesaid handling or manipulating processes are highly time consuming.

SUMMARY OF THE INVENTION

The main object of this invention is to provide a method for use when handling or manipulating organic body fluids which, inter alia, substantially eliminates the risk of contracting diseases, by avoiding any form of contact with the sample. This object is achieved in accordance with the present invention because the stopper is never removed from the vacuum tube, but the vacuum therein is equalized with the aid of a cannula which penetrates the rubber stopper and which permits access to the sample without the risk of the sample running unintentionally from the vacuum tube. This procedure also saves a significant amount of time, in comparison with present day techniques. The invention incorporates a pressure-equalizing and sample-retrieving cannula which comprises a penetrating pipe provided with a pointed end, for penetrating the outer stopper. The other end of the pipe merges with a seating for a transfer pipette, cuvette, or like collecting vessel equipped with a suction hose that extends through the pipe and into the vacuum tube. The seating is an integral part of a holder device that has downwardly protruding holding or fixating means which grip around the stopper and hold said cannula in place, so that the vacuum tube can be centrifuged with the cannula fitted thereto; and the seating is constructed in such a manner to guide accurately and to hold firmly that end of the pipette or cuvette which co-operates with the seating, so that the vacuum tube with the cuvette or pipette fitted thereto can be handled as a unit and connected to a separate pump means for drawing fluid to be analysed into said pipette or cuvette.

A method in accordance with the invention will thus enable sample fluid to be drawn into a pipette or cuvette in a substantially closed system, thereby eliminating the risk of harmful contact with the fluid concerned. Because the vacuum tube can be centrifuged with the cannula fitted, there is afforded when testing blood serum the advantage, inter alia, that blood which splashes onto the bottom surface of the rubber stopper will not contaminate the blood serum, as would otherwise be the case if the cannula were to be forced through the stopper subsequent to centrifugation.

Accordingly, when determining the sedimentation rate of a blood sample, a pipette intended for this purpose is connected to the cannula seating and blood is drawn into the pipette to the level intended, whereafter the pipette and vacuum tube can be placed as a unit in a rack or stand which is intended for reading the blood sedimentation rate. Thus, this is effected completely without touching the sample.

In accordance with one embodiment of the invention, the aforesaid seating comprises an upstanding collar-like member having a conically flared opening which is intended to co-act with a conically tapering end part of a pipette or cuvette, in a manner to detachably lock the pipette or cuvette to the device. The pressure-equalizing cannula is preferably made of an extremely hard plastics material, such as polystyrene or the like, while the pipette or cuvette so-acting with the cannula is made of a much softer material, such as polypropylene or the like. The combination of wedging forces and frictional forces obtained with this construction ensures that the components will be locked firmly together.

The penetrating pipe is suitably cut obliquely in a manner to provide a point at one end thereof, and preferably the pipe material located at least above the part closest to the point is cut away along an arcuate line, so as to reduce the point angle still further. Furthermore, at least the cut pipe-surfaces nearest the pointed end of the pipe are suitably angled in relation to one another, so that as the point penetrates the rubber stopper the rubber material therein is displaced to both sides, therewith to prevent slivers of rubber from being cut away. This is extremely important.

BRIEF DESCRIPTION OF THE DRAWING

The invention will now be described in more detail with reference to exemplifying embodiments thereof illustrated in the accompanying drawings.

FIG. 1 illustrates an exemplifying embodiment of a device according to the invention, together with the components with which it can be used.

FIG. 1A is a view of the pointed end of the cannula, both in perspective and in side view.

FIG. 2 illustrates the device of FIG. 1 while withdrawing a sample for analysis.

FIG. 3 illustrates the device prior to analysing the sample.

FIG. 4 illustrates a device according to the invention together with the components used when determining the sedimentation rate of blood.

FIG. 5 illustrates the device of FIG. 4 while withdrawing a sample for determining the blood sedimentation rate.

DETAILED DESCRIPTION OF THE PREFERRED EMBODIMENTS

In FIG. 1 the reference 1 identifies a so-called vacuum tube which is sealed hermetically by means of a rubber stopper 2. When taking a sample of a patient's blood, blood is drawn from the patient into the tube 1, through a needle-like cannula inserted through the stopper 2. It is assumed in the following description that this stage of the process has been completed and that the tube therefore contains a blood sample.

The need to remove the rubber stopper manually from the vacuum tube in the laboratory, in order to have access to the contents of the tube, which can involve the risk of spreading disease as beforementioned, can be obviated in accordance with the invention by using a pressure-equalizing and sample-retrieving cannula 3, which comprises a penetrating pipe 4 having a pointed end 5. The pipe 4 can be caused to penetrate the stopper 2, either mechanically or with the aid of mechanical devices, so as to achieve controlled equalization between ambient pressure and the pressure in the vacuum tube, while at the same time obtaining access to the sample held in the tube. In order to facilitate penetration of the pointed end of the pipe 4 through the rubber stopper 2, at least that part of the pipe located nearest the pointed end 5 is conveniently cut along an arcuate line, so as to provide, inter alia, a sharper point.

It is extremely important that no part of the stopper is cut away as the pipe 4 penetrates the stopper. Consequently, with this in mind, the cut surfaces 26 nearest the pointed end 5 are angled away from one another in the manner illustrated in FIG. 1A, there being obtained in this way a point configuration which generates a ploughing action as the point passes through the stopper, and therewith causes the rubber material to be pushed to both sides, therewith eliminating, or at least greatly reducing, the risk of pieces of rubber being cut away from the stopper.

Practical tests have shown that no liquid or fluid will run from a vacuum tube 1 when the cannula 3 is fitted in position, not even when the tube is turned upside down. This is due to the pressure differences that prevail when the pipe 4 is surrounded completely with fluid. It was also found that no fluid is able to leave the vacuum tube through the cannula when the vacuum tube lies horizontally or is inclined at some other angle to the vertical. In these latter cases a fluid plug forms in the tube, most likely as a result of the surface tension created between the cannula material and the fluid. Under normal conditions, the pressure within the vacuum tube is unable to force out this fluid plug. The tests showed that fluid can only be induced to leave the tube, and then only in droplet form, by shaking the tube vigorously. This phenomenon enables the cannula 3 to be fitted to the vacuum tube immediately after having taken a sample, so that ready access to the sample can be had when arriving at the laboratory. Since practically all analyses of a blood sample are carried out on the blood serum, apart from blood sedimentation assays, the blood sample must first be centrifuged, in order to separate the blood serum from the blood corpuscles. Accordingly, the cannula according to the invention is constructed so that it can be mounted on the vacuum tube during centrifugation of the sample, this being essential in order to achieve efficient handling of the sample. In addition to rationalizing the process in this way there is obtained the added advantage that fragments of blood which might splash onto the bottom of the rubber stopper 2 during the process of centrifugation will not be carried by the cannula into the separated blood serum, as might be the case when the cannula is not fitted to the vacuum tube until the sample has been centrifuged.

In order to enable the blood sample to be centrifuged with the cannula fitted to the vacuum tube, the cannula 3 of the illustrated embodiment is provided with a downwardly projecting collar 6, which grips around the upper part of the rubber stopper 2 and positively guides and firmly holds the cannula in the rubber stopper. The collar 6, however, it constructed so that air is able to pass between the stopper 2 and the collar 6 when the cannula is fitted. Alternatively, the peripheral surface of the stopper 2 may be grooved or milled.

The reference 7 indicates a plurality of apertures provided at the junction between the flared exit orifice of the pipe 4 and the surrounding collar 6, therewith to enable ambient air to pass into the pipe 4, for reasons explained herebelow.

The cannula 3 is also provided with an upwardly protruding collar 8, which receives the lower part 9 of a collecting vessel, which in the illustrated embodiment consists of a sample cuvette 10. The lower part 9 of the cuvette 10 tapers conically in order to fit accurately into the conically flared seating presented by the collar 8. The wedging action obtained thereby, in combination with the friction forces between the cannula material 3 and the cuvette 9, 10, ensure that these parts of the device are firmly locked together. In this regard it is preferred that the cannula 3 is made of an extremely hard plastics material, such as polystyrene or the like, while the cuvette is made of a much softer plastics material, such as polypropylene or the like. These locking forces can be enhanced by providing axially extending ridges or like promonatories on the mutually abutting surfaces of said lower part 9 and/or the collar 8. If the ridges are provided on the cannula of hard plastics material they can have sharp edges cutting into the other part to prevent relative rotation.

The cuvette 10 illustrated in FIG. 1 is provided with a tubular suction hose 11, the diameter of which is slightly smaller than the diameter of the penetrating pipe 4, such as to enable the hose to be passed through the pipe 4 with a given amount of clearance. Thus, there is obtained an air passage between the suction hose 11 and the inner wall of the pipe 4.

The cuvette 10 is provided with a non-return valve, in the form of a valve body 12 mounted on a resilient, plate-like element 13 which enables the valve body 12 to move between a sealing position, in contact with the valve seating 14, and an open position spaced from the seating. The reference number 15 identifies a filter element for filtering the fluid drawn into the cuvette 10.

The cuvette 10 is provided on its upper end with a bayonet fitting, for attaching the cuvette to a pump means 16. This pump comprises, in a known manner, a plunger 18 which can be depressed against the action of a spring 17, and which generates a suction effect when returned by the force exerted thereon by the spring.

FIG. 2 illustrates the device according to FIG. 1 during the process of drawing a volume of sample into the cuvette 10. In this case, the vacuum tube 1 has first been centrifuged with the cannula 3 in position in the tube, to separate the blood serum 19 from the blood corpuscles 20. The interface between the blood serum and blood corpuscles is normally defined by a gel layer 21 of suitable density, the gel herefore being found in the vacuum tube prior to taking a blood sample. The pump means 16 is then used to draw a given volume of blood serum 19 into the cuvette 10. During this process, air is able to pass into the vacuum tube along the passage defined between the suction hose and the pipe 4. If the level of sample in the vacuum tube 1 is so low as to require the cuvette to be pressed down in the cannula seating, air will be drawn by suction into the tube, via the aforesaid passages defined between the collar 6 and rubber stopper 2, and via the apertures 7.

Subsequent to drawing a desired volume of sample into the cuvette 10, the cuvette is pressed firmly into the seating formed in the cannula 3 by the collar 8 and locked in this position, whereafter the pump 16 can be removed, c.f. FIG. 3. Due to the provision of the non-return valve 12, the volume of sample will be held in the cuvette 10 and can be used immediately for the analyses desired, or can be stored for subsequent analyses. The cuvette 10 and the vacuum tube 1 can therewith be handled as a unit, without any risk of contaminating droplets escaping from the suction hose or the like.

When the sample is to be stored for prolonged periods of time, the cuvette 10 can be sealed by means of a lid provided with a bayonet fitting. This affords an important advantage over present day procedures, in which if a sample is to be stored for subsequent analyses it is necessary to pour the blood-serum part of the separated blood sample into a separate test tube and, if blood corpuscles accompany the serum, re-decant the sample. Such procedures are always accompanied with the risk of infection, and also with the risk of confusing one sample for another. When practising the invention, a sample is always identified by the vacuum tube originally used, since it is not necessary to transfer the sample from one tube to another.

Since the cuvette 10 and the cannula 3 are made from an inexpensive plastics material they can be scrapped together with the vacuum tube 1, subsequent to analysing the sample. The pump 16, on the other hand, can be used repeatedly for sampling procedures, since the pump does not come into contact with the sample fluid.

FIG. 4 illustrates a device which is similar to the device illustrated in FIG. 1 but which is intended for use when determining the rate of sedimentation of blood. Corresponding components have been identified with the same references. As will be seen from the Figures, the single differences between the two embodiments is that the cuvette has been replaced with a holder device 22 for a pipette 23. The holder device 22 is herewith provided with a downwardly projecting, conically tapering part 9 which can be locked firmly in the conically flared seating of the cannula 3, in the manner aforedescribed. The reference 24 identifies a suction device in the form of a compressible ball 24 in which there is provided an aperture 25 which can be closed with the finger of one hand.

When using the device illustrated in FIG. 4, the rubber stopper 2 is perforated with the aid of the pipe 4, in the aforedescribed manner, after which a suction hose 11 connected to the holder device 22 can be inserted down into the cannula and locked in position, as a result of the locking co-action between the part 9 and the collar 8, vide FIG. 5. Blood from the sample contained in the tube 1 can be drawn into the pipette 23, to the desired level, by first compressing the ball 24 and then holding the aperture 25 closed. Air is able to pass down into the tube, through the passage defined by the collar 6 and the rubber stopper 2, the aperture 7 and the space between the suction hose 11 and the inner wall of the pipe 4. The ball 24 can then be removed when placing the combination of pipette 23 and vacuum tube 1 in a rack intended for reading-off the sedimentation rate of the blood, in a manner known per se.

Thus, when using this device the sedimentation rate of the blood can be determined with the aid of a fully closed system, which totally eliminates the risk of contaminating the personnel involved.

In the aforegoing there has been described a preferred embodiment of a cannula arrangement according to the invention. As will be understood by those skilled in this art, the illustrated embodiment can be modified in several respects without departing from the concept of the invention, namely the concept of achieving controlled pressure equalization in the vacuum tube, or test tube, while at the same time providing access to the content of the tube without needing to remove the stopper. For example, the components for fixing the cannula arrangement to the rubber stopper, or to the upper end of a vacuum tube, can be varied as desired, as can also the configuration of the seating for receiving and locking the lower part of a collecting vessel. For example, a snap-in locking arrangement can be used instead of the aforedescribed conical surfaces. These modifications may be required, for example, when applying the invention in conjunction with vacuum tubes, test tubes, and rubber stoppers that are constructed differently to those described and illustrated, and when applying the invention in conjunction with other types of vessels for collecting sample volumes.

What is claimed is:

1. A method for the analysis of organic body fluids, comprising the steps of:
   (a) a drawing a sample of an organic body fluid from a patient into a hermetically sealed vacuum tube (1) by suction,
   (b) inserting a cannula (3) through a rubber stopper (2) sealing an open end of said tube to equalize a remaining partial vacuum in the tube,
   (c) introducing a suction hose (11) into the tube through the cannula,
   (d) withdrawing a desired quantity of sample fluid from the tube through the suction hose,
   (e) passing said sample quantity to a container (10:23) intended therefor, and
   (f) simultaneously with steps (d) and (e) allowing air to pass down into the vacuum tube to displace the withdrawn sample fluid.

2. A method according to claim 1, further comprising centrifuging the vacuum tube, subsequent to inserting the cannula thereinto, to mutually various components of the sample in said tube, and wherein the suction hose is introduced into the tube to a depth corresponding to a position of a fraction to be analysed.

3. A method according to claims 1 or 2, further comprising retaining the vacuum tube and the container receiving said sample quantity together during the analysis procedure so that the sample is identified by an identification of the tube.

4. A method according to claims 1 or 2, further comprising selecting said container from a group including a receptacle (10) having a non-return valve (12) and a pipette (23) intended for determining a bloodsettling count.

5. A method according to claim 4, further comprising securing the container or pipette to the cannula inserted into the vacuum tube, so that the withdrawn sample quantity can be positively identified by an identification of the vacuum tube.

6. A method for the analysis of organic body fluids, comprising the steps of:

(a) drawing a sample of an organic body fluid from a patient into a hermetically sealed vacuum tube (1) by suction, (b) inserting a cannula (3) through a rubber stopper (2) sealing an open end of said tube to equalize a remaining partial vacuum in the tube, (c) introducing a suction hose (11) into the tube through the cannula, (d) withdrawing a desired quantity of sample fluid from the tube through the suction hose, (e) passing said sample quantity to a container (10;23) intended therefor, and (f) simultaneously with steps (d) and (e) allowing air to pass down into the vacuum tube to displace the withdrawn sample fluid, further comprising centrifuging the vacuum tube to mutually separate various components of the sample in said tube, and wherein the suction hose is introduced into the tube to a depth corresponding to a position of a fraction to be analysed.

* * * * *